(12) United States Patent
Fewkes et al.

(10) Patent No.: US 11,643,630 B2
(45) Date of Patent: May 9, 2023

(54) ILLUMINATED CONTAINER FOR GROWTH OF BIOLOGICAL ENTITIES

(71) Applicant: Corning Incorporated, Corning, NY (US)

(72) Inventors: Edward John Fewkes, Corning, NY (US); Stephan Lvovich Logunov, Corning, NY (US)

(73) Assignee: CORNING INCORPORATED, Corning, NY (US)

( * ) Notice: Subject to any disclaimer, the term of this patent is extended or adjusted under 35 U.S.C. 154(b) by 509 days.

(21) Appl. No.: 15/776,206

(22) PCT Filed: Nov. 18, 2016

(86) PCT No.: PCT/US2016/062751
§ 371 (c)(1),
(2) Date: May 15, 2018

(87) PCT Pub. No.: WO2017/087790
PCT Pub. Date: May 26, 2017

(65) Prior Publication Data
US 2020/0255787 A1   Aug. 13, 2020

Related U.S. Application Data

(60) Provisional application No. 62/303,044, filed on Mar. 3, 2016, provisional application No. 62/303,032, filed
(Continued)

(51) Int. Cl.
*C12M 1/00* (2006.01)
*C12M 1/22* (2006.01)
(Continued)

(52) U.S. Cl.
CPC ............ *C12M 31/08* (2013.01); *C12M 21/02* (2013.01); *C12M 23/10* (2013.01); *C12M 23/14* (2013.01);
(Continued)

(58) Field of Classification Search
CPC ...... C12M 21/02; C12M 31/08; C12M 23/10; C12M 23/14; C12M 23/26; C12M 23/28;
(Continued)

(56) References Cited

U.S. PATENT DOCUMENTS 5,245,404 A     9/1993  Jannson et al.
5,250,095 A  *  10/1993  Sigel, Jr. ............... C03C 13/005
                                                            65/378

(Continued)

FOREIGN PATENT DOCUMENTS

CN     102382754 A     3/2012
CN     102667551 A     9/2012
(Continued)

OTHER PUBLICATIONS

Diekmann, S. et al., "Single Use Bioreactors for the Clinical Production of Monoclonal Antibodies—A Study to Analyze the Performance of a Cho Cell Line and the Quality of the Produced Monoclonal Antibody." BMC Proceedings, vol. 5 (Suppl. 8), pp. 1-5, Nov. 22, 2011.
(Continued)

*Primary Examiner* — Lydia Edwards
(74) *Attorney, Agent, or Firm* — Michael G. Panian

(57) ABSTRACT

An illuminated container for the growth of biological entities is provided. The container is illuminated by a flexible light diffusing fiber. The light diffusing fiber includes a core formed from a silica-based glass and a cladding in direct contact with the core. The light diffusing fiber also includes an outer polymer coating layer surrounding the cladding, the
(Continued)

outer polymer coating layer being the cured product of a liquid polymer blend including a scattering material and a luminophore.

23 Claims, 5 Drawing Sheets

Related U.S. Application Data on Mar. 3, 2016, provisional application No. 62/275,342, filed on Jan. 6, 2016, provisional application No. 62/257,913, filed on Nov. 20, 2015.

(51) Int. Cl.
    *G02B 6/02*     (2006.01)
    *F21V 8/00*     (2006.01)

(52) U.S. Cl.
    CPC ............ *C12M 23/26* (2013.01); *C12M 23/28* (2013.01); *G02B 6/0003* (2013.01); *G02B 6/02338* (2013.01); *G02B 6/02395* (2013.01)

(58) Field of Classification Search
    CPC .............. G02B 6/02395; G02B 6/0003; G02B 6/02338; G02B 6/001
    See application file for complete search history.

(56) References Cited

U.S. PATENT DOCUMENTS

| | | | |
|---|---|---|---|
| 5,737,472 A | 4/1998 | Bernasson et al. | |
| 5,776,235 A | 7/1998 | Camilletti et al. | |
| 6,044,191 A | 3/2000 | Berkey et al. | |
| 6,259,855 B1 | 7/2001 | Lundin | |
| 7,274,847 B2 | 9/2007 | Gowda et al. | |
| 7,386,203 B2 | 6/2008 | Maitland et al. | |
| 7,450,806 B2 | 11/2008 | Bookbinder et al. | |
| 7,609,927 B2 | 10/2009 | Gowda et al. | |
| 8,408,029 B2 | 4/2013 | De Angelis et al. | |
| 8,449,147 B2 | 5/2013 | Papac et al. | |
| 8,481,304 B2 | 7/2013 | Woerlee et al. | |
| 8,492,448 B2 | 7/2013 | Dewa et al. | |
| 8,506,886 B2 | 8/2013 | Owen et al. | |
| 8,545,076 B2 | 10/2013 | Bickham et al. | |
| 8,591,087 B2 | 11/2013 | Bickham et al. | |
| 8,620,125 B2 | 12/2013 | Button et al. | |
| 8,622,625 B2 | 1/2014 | Benjamin et al. | |
| 8,683,827 B2 | 4/2014 | De Angelis et al. | |
| 8,724,942 B2 | 5/2014 | Logunov | |
| 8,787,717 B2 | 7/2014 | Logunov | |
| 8,805,141 B2 | 8/2014 | Fewkes et al. | |
| 8,897,612 B2 | 11/2014 | Logunov | |
| 8,926,143 B2 | 1/2015 | Li et al. | |
| 8,929,703 B2 | 1/2015 | Logunov et al. | |
| 8,998,471 B2 | 4/2015 | Genier | |
| 9,025,923 B2 | 5/2015 | Logunov et al. | |
| 9,093,003 B2 | 7/2015 | Logunov et al. | |
| 9,146,347 B2 | 9/2015 | Logunov et al. | |
| 9,541,694 B2 | 1/2017 | Tissot | |
| 2003/0113082 A1 | 6/2003 | Neuberger | |
| 2005/0074216 A1 | 4/2005 | Irie | |
| 2007/0104437 A1 | 5/2007 | Bookbinder et al. | |
| 2007/0108900 A1 | 5/2007 | Boek | |
| 2009/0148931 A1 | 6/2009 | Wilkerson et al. | |
| 2010/0053970 A1 | 3/2010 | Sato et al. | |
| 2010/0066254 A1 | 3/2010 | Ott et al. | |
| 2010/0283036 A1* | 11/2010 | Coe-Sullivan ...... | H01L 51/5088 257/13 |
| 2011/0037949 A1 | 2/2011 | Papac et al. | |
| 2011/0103757 A1 | 5/2011 | Alkemper et al. | |
| 2011/0122646 A1 | 5/2011 | Bickham et al. | |
| 2011/0188261 A1 | 8/2011 | Deng et al. | |
| 2011/0275180 A1 | 11/2011 | Lin et al. | |
| 2012/0275180 A1 | 11/2012 | Button et al. | |
| 2013/0010456 A1 | 1/2013 | Ishii et al. | |
| 2013/0040372 A1 | 2/2013 | Roell et al. | |
| 2013/0088888 A1 | 4/2013 | Fewkes et al. | |
| 2013/0090402 A1 | 4/2013 | Dewa et al. | |
| 2013/0107565 A1 | 5/2013 | Genier | |
| 2013/0156391 A1 | 6/2013 | Logunov et al. | |
| 2013/0156392 A1 | 6/2013 | Logunov et al. | |
| 2013/0272014 A1 | 10/2013 | Logunov et al. | |
| 2014/0198520 A1 | 7/2014 | Bennett et al. | |
| 2014/0218958 A1 | 8/2014 | Fewkes et al. | |
| 2014/0268815 A1 | 9/2014 | Li et al. | |
| 2014/0355295 A1 | 12/2014 | Kuchinsky | |
| 2015/0062954 A1 | 3/2015 | Crossland et al. | |
| 2015/0369986 A1 | 12/2015 | Logunov et al. | |
| 2017/0212292 A1 | 7/2017 | Brada | |

FOREIGN PATENT DOCUMENTS

| | | |
|---|---|---|
| CN | 103517978 A | 1/2014 |
| DE | 29819259 U1 | 12/1999 |
| DE | 102008009138 A1 | 8/2009 |
| JP | 63-183063 A | 7/1988 |
| JP | 2308786 A | 12/1990 |
| JP | 4000824 B2 | 1/1992 |
| JP | 4091781 A | 3/1992 |
| JP | 05-058094 U | 8/1993 |
| JP | 5058094 B2 | 8/1993 |
| JP | 8066462 A | 3/1996 |
| JP | 9099921 A | 4/1997 |
| JP | 2009198706 A | 9/2009 |
| JP | 2010-530757 A | 9/2010 |
| JP | 2013-511749 A | 4/2013 |
| JP | 2014-534566 A | 12/2014 |
| JP | 2015-507763 A | 3/2015 |
| WO | 200079319 A1 | 12/2000 |
| WO | 2009069967 A2 | 6/2009 |
| WO | 2010011299 A2 | 1/2010 |
| WO | 2015/031299 A2 | 3/2015 |
| WO | 2015/031551 A1 | 3/2015 |

OTHER PUBLICATIONS

Engelke, H. et al., "Control of Protein Function Through Optochemcial Translocation." ACS Synthetic Biology, 2014, vol. 3, pp. 731-736, Feb. 4, 2014.
Wikipedia Contributors, "Single-Use Bioreactor." Wikipedia: The Free Encyclopedia, http://en.wikipedia.org/wiki/Single-use_bioreactor, 3 Pages, Last Edited May 19, 2018.
International Search Report and Written Opinion of the International Searching Authority; PCT/US2016/062751; dated Jan. 27, 2017; 11 Pages; European Patent Office.
Kushibiki, T. et al., "Optogenetics: Novel Tools for Controlling Mammalian Cell Functions With Light." International Journal of Photoenergy, vol. 2014, pp. 1-10, Apr. 28, 2014.
Mullan, B. et al., "Transfer, Implementation and Late Stage Development of an End-to-End Single-Use Process for Monoclonal Antibody Manufacture." American Pharmaceutical Review, 7 Pages, Jan. 1, 2011.
Smelko, J. et al., "Performance of High Intensity FED-Batch Mammalian Cell Cultures in Disposable Bioreactor Systems." Biotechnology Progress, vol. 27, No. 5, pp. 1358-1364, May 27, 2011.
Stoien, J. et al., "Effect of Near-Ultraviolet and Visible Light On Mammalian Cells in Culture II. Formation of Toxic Photoproducts in Tissue Culture Medium by Blacklight." Proceedings of National Academy Sciences of the USA, vol. 71, No. 10, pp. 3961-3965, Oct. 1974.
Young, D. et al., "Light-Activation of Gene Function in Mammalian Cells via Ribozymes." Chemical Communications, Issue 5, pp. 568-570, Dec. 2, 2008.
Fewkes et al., "Light Converting Coating for Light Diffusing Device." Filed as U.S. Appl. No. 15/776,199, filed May 15, 2018; 31 Pages.
Barabanenkov, Y., et al., "Status of the Theroy of Propagation of Waves in Randomly Inhomogeneous Medium." Soviet Phsyics Uspekhi, vol. 13, No. 5, pp. 551-575, Sep. 1970.

(56) References Cited

OTHER PUBLICATIONS

Bohren, C. et al., "Absorption and Scattering of Light by Small Particles, Chapter 8: A Potpourri of Particles." A Wiley-Interscience Ppublication, pp. 194-208, 1998.

Endruweit, E., et al., "Spectoscopic Experiementes Regarding the Efficiency of Side Emission Optical Fibres in the UV-A and Visible Blue Spectrum." Optics and Lasers Engineering, vol. 46, pp. 97-105, Oct. 24, 2007.

Huang, H., et al., "Planar Lighting System Using Array of Blue LED's to Excite Yellow Remote Phosphor Film." Journal of Display Technology, vol. 7, No. 1, pp. 44-51, Jan. 2011.

Smith, T., et al., "The C.I.E. Colorimetric Standards and Their Use." Transactions of the Optical Society, vol. 33, No. 3, pp. 73-134, 1931.

Spencer, G., et al., "General Ray-Tracing Prodedure." Journal of the Optical Society of America, vol. 52, No. 6, pp. 672-678, Jun. 1962.

Taflove, A., et al., "Computational Electrodynamics: The Finite-Difference Time Domain Method, Chapter 3: Introduction to Maxwell's Equation and the Tee Algorithm." Artech House, Second Edition, pp. 76-89, 2000.

Van De Hulst, H., "Light Scattering by Small Particles, Chapter 15: Circular Cylinders." Dover Publications, pp. 297-302, 1957.

European Patent Application No. 16816780.7, Communication pursuant to Article 94(3) EPC dated Dec. 1, 2020; 4 Pages; European Patent Office.

English Translation of JP2018526098 Office Action dated Jul. 29, 2020; 4 Pages; Japanese Patent Office.

Matsunaga et al; "Glutamate Production From CO2 by Marine Cyanobacterium *Synechococcus* Sp. Using a Novel Biosolar Reactor Employing Light-Diffusing Optical Fibers"; Applied Biochemistry and Biotechnology; 1991; 28/29 pp. 157-167.

Chinese Patent Application No. 201680068020.X, Office Action dated Apr. 8, 2021, 9 pages (5 pages of English Translation and 4 pages of Original Document), Chinese Patent Office.

Japanese Patent Application No. 2018-526098 Office Action dated Jun. 2, 2021, 5 pages (2 pages of English Translation and 3 pages of Original Document); Japanese Patent Office.

"Concentrated Light", Middle Volume, 1982, 11 pages (6 pages of English Translation and 5 pages of Original Document).

Chinese Patent Application No. 201680068020.X, Office Action dated Sep. 28, 2021, 9 pages (8 pages of English Translation and 1 page of Original Document), Chinese Patent Office.

\* cited by examiner

ILLUMINATED CONTAINER FOR GROWTH OF BIOLOGICAL ENTITIES

CROSS-REFERENCE TO RELATED APPLICATIONS

This is a national stage application under 35 U.S.C. § 371 of International Application No. PCT/US2016/062751, filed on Nov. 18, 2016, which claims the benefit of priority of U.S. Provisional Application Ser. No. 62/257,913 filed on Nov. 20, 2015, U.S. Provisional Application Ser. No. 62/275,342 filed on Jan. 6, 2016, U.S. Provisional Application Ser. No. 62/303,032 filed on Mar. 3, 2016, and U.S. Provisional Application Ser. No. 62/303,044 filed on Mar. 3, 2016 the content of which is relied upon and incorporated herein by reference in its entirety.

FIELD

The present disclosure relates generally to light diffusing optical fiber for use in illumination applications such as the growth of biological entities, and, more particularly, to light diffusing optical fiber having color converting coatings.

BACKGROUND

Optical fiber that emit light radially outward along the length of the fiber, thereby illuminating the fiber, are particularly useful for a wide array of applications, such as special lighting, photochemistry, and for use in electronics and display devices. Such light diffusing fiber (referred to herein as "LDF") have been used to successfully demonstrate the emission of light of various colors. Light sources capable of emitting electromagnetic radiation that is in the visible light range of wavelengths may be coupled to the LDF to introduce light having different colors into the LDF. Such colored light is then emitted along the length of the LDF. However, light sources capable of emitting light of certain colors can be expensive and can make their use cost prohibitive in many LDF applications.

As an alternative, a luminophore (an atom or chemical compound that manifests luminescence, and includes a variety of fluorophores and phosphors) may be disposed on a surface of the LDF. Often, a coating layer including the luminophore is disposed on a surface of the LDF surrounding one more other coating layers. Electromagnetic radiation emitted from a light source at a first wavelength may interact with the luminophore and be converted to a second wavelength in the visible light range of wavelengths. Similar to the previous discussion, the light source may be chosen based on the wavelength of the light emitted from the light source. Additionally, the luminophore may be chosen based on the intended wavelength of the light emitted along the length of the LDF. In this manner, light having a predetermined color may be emitted along the length of the LDF. However, luminophore materials used for this purpose can be difficult to mix with coating polymers in high concentrations. As a result, it is conventionally necessary for the coating having the luminophore materials to be thick enough to enable adequate light conversion. For example, where conventional LDF has an outer diameter of about 250 μm, the thickness added by a coating including a luminophore may increase the LDF outer diameter to about 500 μm or greater. Such luminophore materials are conventionally expensive and forming coatings thick enough to enable adequate light conversion can be cost prohibitive in LDF applications where low costs are expected.

Bioreactors are used to grow cells. Mammalian cells are grown in bioreactors to produce quantities of cells, proteins or other products. Non-mammalian cells are grown in bioreactors, in some instances to produce products including alcohol and biofuels. In some instances, non-mammalian cells require light as a part of their growth and culture. Efficient, economical and reliable light sources in bioreactors may be desirable.

SUMMARY

According to an embodiment of the present disclosure, a light diffusing fiber having a core formed from a silica-based glass and a cladding in direct contact with the core is provided, in a container for the growth of biological entities. For example, a light diffusing fiber may be used in a biological container such as a well, a flask, a dish, a bag, a tank, a multi-layered flask, a bioreactor, a single use bioreactor, or a similar container. The light diffusing fiber also includes an outer polymer coating layer surrounding the cladding, the outer polymer coating layer being the cured product of a liquid polymer blend including a scattering material and a luminophore.

According to another embodiment, the light diffusing fiber, provided in a container for the growth of biological entities may be a fiber that is tunable to provide a desired wavelength of light. In embodiments, the wavelength of light is tuned to maximize the biological processes of the cells in culture in the container.

In another embodiment, the light may be delivered directly to aqueous media contained in a container for the growth of biological entities.

According to another embodiment of the present disclosure, a method for forming a light diffusing fiber is provided. The method includes forming an optical fiber preform having a silica-based glass preform core and drawing the optical fiber preform to form an optical fiber. The method further includes coating the optical fiber with a liquid polymer blend including a scattering material and a luminophore, and curing the liquid polymer blend to form an outer polymer coating layer.

Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary, and are intended to provide an overview or framework to understanding the nature and character of the claims. The accompanying drawings are included to provide a further understanding, and are incorporated in and constitute a part of this specification. The drawings illustrate one or more embodiment(s), and together with the description serve to explain principles and operation of the various embodiments.

BRIEF DESCRIPTION OF THE DRAWINGS

The disclosure will be understood more clearly from the following description and from the accompanying figures, given purely by way of non-limiting example, in which.

DETAILED DESCRIPTION

Figure 1:
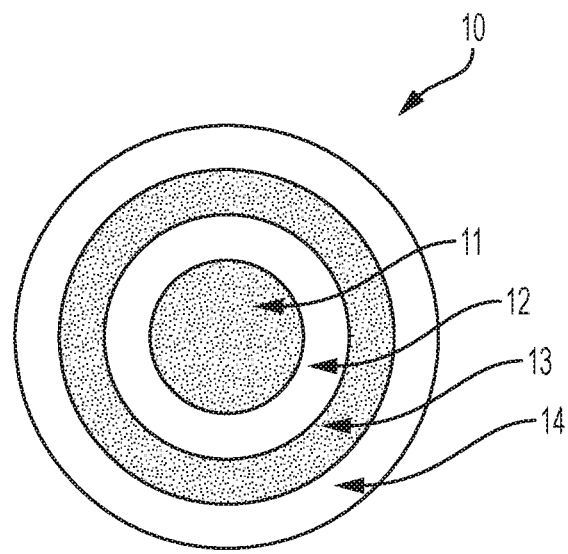
FIG. 1 illustrates a cross section of a conventional LDF.

Reference will now be made in detail to the present embodiment(s), an example(s) of which is/are illustrated in the accompanying drawings. Whenever possible, the same reference numerals will be used throughout the drawings to refer to the same or like parts.

The singular forms "a," "an" and "the" include plural referents unless the context clearly dictates otherwise. The endpoints of all ranges reciting the same characteristic are independently combinable and inclusive of the recited endpoint. All references are incorporated herein by reference.

The present disclosure is described below, at first generally, then in detail on the basis of several exemplary embodiments. The features shown in combination with one another in the individual exemplary embodiments do not all have to be realized. In particular, individual features may also be omitted or combined in some other way with other features shown of the same exemplary embodiment or else of other exemplary embodiments.

The term "light diffusing fiber" (LDF) refers to a flexible optical waveguide, such as an optical fiber, employing nano-sized structures that are utilized to scatter or diffuse light out of the sides of the fiber, such that light is guided away from the core of the waveguide and through the outer surfaces of the waveguide to provide illumination. Concepts relevant to the underlying principles of the claimed subject matter are disclosed in U.S. Patent Application Publication No. US 2011/0122646 A1, which is incorporated in its entirety herein by reference.

As used herein, the term "nano-structured fiber region" describes a region or area of a fiber with a large number of gas filled voids, or other nano-sized structures. The region or area may have, for example, more than 50 voids, or more than 100 voids, or even more than 200 voids in the cross-section of the fiber. The gas filled voids may contain, for example, $SO_2$, Kr, Ar, $CO_2$, $N_2$, $O_2$, or mixture thereof. The cross-sectional size (e.g., diameter) of nano-sized structures (e.g., voids) as described herein may vary from about 10 nm to about 1.0 µm (for example, from about 50 nm to about 500 nm), and the length may vary from about 1.0 millimeter to about 50 meters (for example, from about 2.0 mm to about 5.0 meters, or from about 5.0 mm to about 1.0 meter).

LDF as described has good angular scattering properties (uniform dissipation of light away from the axis of the fiber) and good bending performance to avoid bright spots at fiber bends. A desirable attribute of at least some of the embodiments described herein is uniform and high illumination along the length of the fiber. Because the optical fiber is flexible, it allows a wide variety of the shapes to be deployed. The LDF described herein may have no bright spots (due to elevated bend losses) at the bending points of the fiber, such that the illumination provided by the fiber does not vary by more than about 40%. The variation of the illumination provided by the fiber may be less than about 30%, or less than about 20% or even less than about 10%. For example, in at least some embodiments, the average scattering loss of the fiber is greater than about 50 dB/km, and the scattering loss does not vary by more than about 40% (i.e., the scattering loss is within ±40% of the average scattering loss) over any given fiber segment having a length of about 0.2 meters. The average scattering loss of the fiber may be greater than about 50 dB/km with the scattering loss varying by less than about 40% over fiber segments having a length of less than about 0.05 meters. The average scattering loss of the fiber may be greater than about 50 dB/km with the scattering loss varying by less than about 40% over fiber segments having a length of about 0.01 meters. The average scattering loss of the fiber may also be greater than about 50 dB/km with the scattering loss varying by less than about 30%, or less than 20%, or even less than about 10%, over fiber segments having a length of about 0.01 meters.

According to embodiments of the present disclosure, the intensity variation of the integrated light intensity diffused through sides of the fiber at the illumination wavelength is less than about 40% for the target length of the fiber, which can be, for example, between about 0.02 meters to about 100 meters. The light diffusing fiber described herein may produce uniform illumination along the entire length of the fiber or uniform illumination along a segment of the fiber which is less than the entire length of the fiber. As used herein, the term "uniform illumination," means that the intensity of light emitted from the light diffusing fiber does not vary by more than 25% over the specified length.

LDF designs described herein include a nano-structured fiber region (region with nano-sized structures) placed in the core area of the fiber, or very close to the core. The LDF have scattering losses in excess of about 50 dB/km, for example, greater than about 100 dB/km, greater than about 200 dB/km, greater than about 300 dB/km, greater than about 325 dB/km, greater than about 500 dB/km, greater than about 1000 dB/km, greater than about 3000 dB/km, or even greater than about 5000 dB/km. The scattering loss, and thus illumination, or light radiated by the fiber, is uniform in angular space.

In order to reduce or to eliminate bright spots at bends in the fiber, it is desirable that the increase in attenuation at a 90° bend in the fiber is less than about 5.0 dB/turn, for example, less than about 3.0 dB/turn, less than about 2.0 dB/turn, or even less than about 1.0 dB/turn when the bend diameter is less than about 50 mm. In exemplary embodiments, these low bend losses are achieved at even smaller bend diameters, for example, at bend diameters of less than about 20 mm, less than about 10 mm, or even less than about 5.0 mm. The total increase in attenuation may be less than about 1.0 dB per 90 degree turn at a bend radius of about 5.0 mm.

The bending loss is equal to or is less than the intrinsic scattering loss from the core of the straight fiber. The intrinsic scattering is predominantly due to scattering from the nano-sized structures. Thus, according to at least the bend insensitive embodiments of optical fiber, the bend loss does not exceed the intrinsic scattering of the fiber. However, because scattering level is a function of bending diameter, the bending deployment of the fiber depends on its scattering level. For example, the fiber may have a bend loss of less than about 3.0 dB/turn, or even less than about 2.0 dB/turn, and the fiber can be bent in an arc with a radius as small as about 5.0 mm without forming bright spots.

FIG. 1 illustrates an example of a conventional light diffusing fiber. As shown, the LDF 10 includes a core portion 11 and a cladding 12 which surrounds and is in direct contact with the core portion 11. The LDF 10 also includes a scattering coating layer 13 which surrounds and is in direct contact with the cladding 12 and a separate phosphor coating layer 14 which surrounds the scattering coating layer 13. Because of the separate coating layers, such conventional LDF may have an outer diameter of greater than about 250 µm and commonly has an outer diameter of about 500 µm or greater.

Figure 2:
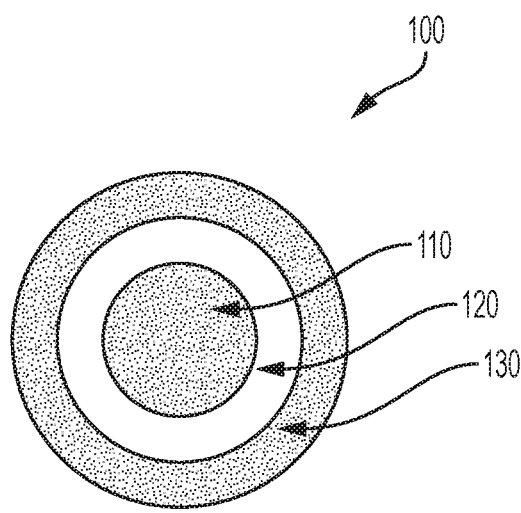
FIG. 2 illustrates a cross section of an LDF in accordance with the present disclosure.

FIG. 2 illustrates an exemplary light diffusing fiber. The LDF 100 includes a core portion 110 having an outer radius of greater than about 10 µm and less than about 250 µm, for example, between about 25 µm and about 200 µm, or between about 30 µm and about 100 µm. According to embodiments of the present disclosure, the core portion 110 includes voids that scatter light propagating in the core portion 110 such that the light is directed radially outward from the core portion 110, thereby illuminating the LDF and the space surrounding the LDF. The scatter-induced attenuation may be increased through increasing the concentration of voids, positioning voids throughout the fiber, or in cases where the voids are limited to an annular ring, increasing the width of the void-containing ring will also increase the scattering-induced attenuation for the same density of voids. Additionally, in compositions where the voids are helical, the scattering-induced attenuation may also be increased by varying the pitch of the helical voids over the length of the fiber.

Still referring to FIG. 2, the LDF 100 may further include a cladding 120 which surrounds and is in direct contact with the core portion 110. The cladding 120 may be formed from a material which has a relatively low refractive index in order to increase the numerical aperture (NA) of the LDF 100. The numerical aperture of the fiber may be greater than about 0.3, and in some embodiments greater than about 0.4. The cladding 120 may include a low index polymeric material such as UV or thermally curable fluoroacrylate, such as PC452 available from SSCP Co. Ltd 403-2, Moknae, Ansan, Kyunggi, Korea, or silicone. Such low index polymer cladding may have a relative refractive index that is negative relative to pure undoped silica. For example, the relative refractive index of the low index polymer cladding may be less than about −0.5%, or even less than about −1.0%. Also, the cladding 120 may include a high modulus coating. Alternatively, the cladding 120 may include a silica glass. According to embodiments of the present disclosure, the silica glass in the cladding may be down-doped with a down-dopant, such as, for example, fluorine. As used herein, the term "down-dopant" refers to a dopant which has a propensity to lower the refractive index relative to pure undoped silica. The cladding 120 generally has an index of refraction which is less than the index of refraction of the core portion 110.

The cladding 120 generally extends from the outer radius of the core portion 110. The radial width of the cladding 120 may be greater than about 1.0 µm. For example, the radial width of the cladding 120 may be between about 5.0 µm and about 300 µm, such as less than about 200 µm. The radial width of the cladding 120 may also be, for example, between about 2.0 µm and about 100 µm, between about 2.0 µm and about 50 µm, between at least 2.0 µm and about 20 µm, or even between about 2.0 µm and about 12 µm. The radial width of the cladding 120 may be, for example, at least about 7.0 µm.

Referring again to FIG. 2, the LDF 100 further includes an outer polymer coating layer 130 which surrounds and is in direct contact with the cladding 120. As used herein, the term "outer polymer coating layer" is meant only to relate the position of the polymer coating layer to the light diffusing device and is not meant to designate the polymer coating as being the outermost coating layer of the coated light diffusing device. It should be understood that embodiments of the present disclosure contemplate coated light diffusing devices having one or more additional coatings, for example protective coatings, that surround the outer polymer coating layer 130. The LDF 100 may also include an optional coating between the cladding 120 and the outer polymer coating layer 130. The optional coating is a low modulus material that may be included to better protect the glass portions of the light-diffusing fiber by dissipating mechanical disturbances transmitted through the outer polymer coating layer 130 when the light-diffusing fiber is subjected to an external force. When present, the optional coating surrounds and contacts the cladding 120. In one embodiment, the optional coating is the cured product of a composition that includes a curable crosslinker, a curable diluent, and a polymerization initiator. The composition may include one or more curable crosslinkers, one or more curable diluents, and/or one or more polymerization initiators. In one embodiment, the curable crosslinker is essentially free of urethane and urea functional groups. When present, the optional coating has a lower refractive index than the outer polymer coating.

The outer polymer coating 130 includes a scattering material and a luminophore. The outer polymer coating layer 130 may include a polymer material that may be any liquid polymer or prepolymer material into which a scattering composition (which includes the scattering material) and the luminophore could be added and in which the blend may be applied to the fiber as a liquid and then converted to a solid after application to the fiber. In some embodiments, the outer polymer coating layer 130 is formed from a polymer material such as an acrylate-based polymer or silicone-based polymer.

The scattering composition may be, for example, a dispersion which includes a scattering material and which is added to the liquid polymer blend. The concentration of the scattering composition in the liquid polymer blend of the outer polymer coating may be between about 5.0 wt. % and about 80 wt. %. For example, the concentration of the scattering composition in the liquid polymer blend of the outer polymer coating may be between about 10 wt. % and about 70 wt. %, or between about 20 wt. % and about 60 wt. %, or even between about 30 wt. % and about 60 wt. %.

The scattering material may include nano- or microparticles with an average diameter of from about 200 nm to about 10 µm. For example, the average diameter of the particles may be between about 400 nm and about 8.0 µm, or even between about 100 nm and about 6.0 µm. The nano- or microparticles may be particles of a metal oxide or of other high refractive index materials, such as, but not limited to, $TiO_2$, $ZnO$, $SiO_2$, $BaS$, $MgO$, $Al_2O_3$ or $Zr$. The scattering material may include $TiO_2$-based particles, and the scattering composition may be, for example, a white ink dispersion, which provides for an angle independent distribution of light scattered from the core portion 110 of the light diffusing optical fiber 100. The concentration of the particles of the scattering material may vary along the length of the fiber or may be constant and may be a weight percent sufficient to provide even scattering of the light while limiting overall attenuation. The concentration of the particles of the scattering material may be greater than about 0.5 wt. %. For example, the concentration of the particles of the scattering material may be greater than about 1.0 wt. %, or greater than about 1.25 wt. %, or greater than about 1.5 wt. %, or greater than about 2.0 wt. %, or greater than about 2.5 wt. %, or greater than about 3.0 wt. %, or greater than about 3.5 wt. %, or even greater than about 4.0 wt. %. The concentration of the particles of the scattering material may be between about 0.5 wt. % and about 10 wt. %, or between about 1.0 wt. % and about 10 wt. %, or between about 1.25 wt. % and about 7.5 wt. %, or between about 1.25 wt. % and about 6.0 wt. %, or between about 1.5 wt. % and about 10 wt. %, or between about 1.5 wt. % and about 7.5 wt. %, or between about 1.5 wt. % and about 6.0 wt. %, or between about 2.0 wt. % and about 10 wt. %, or between about 2.0 wt. % and about 7.5 wt. %, or even between about 2.0 wt. % and about 6.0 wt. %. The scattering material may also include nano- or microsized particles or voids of low refractive index, such as gas bubbles.

The luminophore may include a fluorescent or phosphorescent material which may be any organic or inorganic fluorescent or phosphorescent material or a mixture of any organic or inorganic fluorescent or phosphorescent materials. For example, the luminophore may include, but is not limited to, Ce-doped YAG, Nd-doped YAG, rare earth oxide materials, quantum dots such as CdS, CdS/ZnS, InP, nanoparticles, metal-enhanced fluorescence of organic fluorophores, etc. The concentration of luminophore in the liquid polymer blend of the outer polymer coating may be controlled to provide desired color coordinates x and y in CIE color space diagram. The concentration of the luminophore in the liquid polymer blend of the outer polymer coating may be between about 10 wt. % and about 50 wt. %. For example, the concentration of the luminophore in the liquid polymer blend of the outer polymer coating may be between about 15 wt. % and about 45 wt. %, or between about 25 wt. % and about 40 wt. %, or even between about 30 wt. % and about 35 wt. %.

The outer polymer coating layer 130 generally extends from the outer radius of the cladding 120. The radial width of the outer polymer coating layer 130 may be between about 1.0 µm and about 450 µm, for example, between about 20 µm and about 300 µm, or even between about 40 µm and about 90 µm. The radial width of LDF designs according to embodiments of the present disclosure may be limited such that the outer diameter of the LDF is less than or equal to about 500 µm, or less than or equal to about 400 µm, or even less than or equal to about 300 µm.

Because the outer polymer coating layer 130 includes both a scattering material and a luminophore, the outer polymer coating layer 130 enhances the distribution and/or the nature of the light emitted radially from the core portion 110 and converts light emitted radially from the core portion 110 to a longer wavelength of light. The efficiency of the luminophore to convert light is known to be related to luminophore concentration and to the amount of the luminophore-containing material (i.e. thickness or volume of the material). Generally, promotion of an electron to a higher energy level, or excitation, occurs upon absorption of a photon (an "excitation photon"), and adequate light conversion is related to the period of time (i.e.: the number of interactions between the excitation photon and the luminophore) which the excitation photon interacts with the luminophore. As such, the number of interactions between the excitation photons and the luminophore is proportional to the concentration of the luminophore and the thickness of the luminophore-containing material. Typical conversion efficiency for a single interaction is greater than about 90%. Conventionally, to enable adequate light conversion in light diffusing optical fiber, luminophore concentration and/or thickness of luminophore-containing coatings are increased. However, because it can be difficult to mix high luminophore concentrations with coating polymers, enabling adequate light conversion is conventionally achieved by increasing the thickness of luminophore-containing coatings on the fiber. Without wishing to be limited by any particular theory, it is believed that including both a scattering material and a luminophore in the same coating layer increases the path length of the excitation photon independently of coating thickness, which in turn effectively reduces the thickness of the coating layer. LDF having greater than about 0 wt. % scattering material in the outer polymer coating layer 130 displayed a path length of the excitation photon that was greater than the actual thickness of the polymer coating layer 130. In particular, LDF having about 0.50 wt. % or greater of scattering material in the outer polymer coating layer 130 displayed a path length of the excitation photon that was greater than about 2.0 times the actual thickness of the polymer coating 130.

Figure 3:
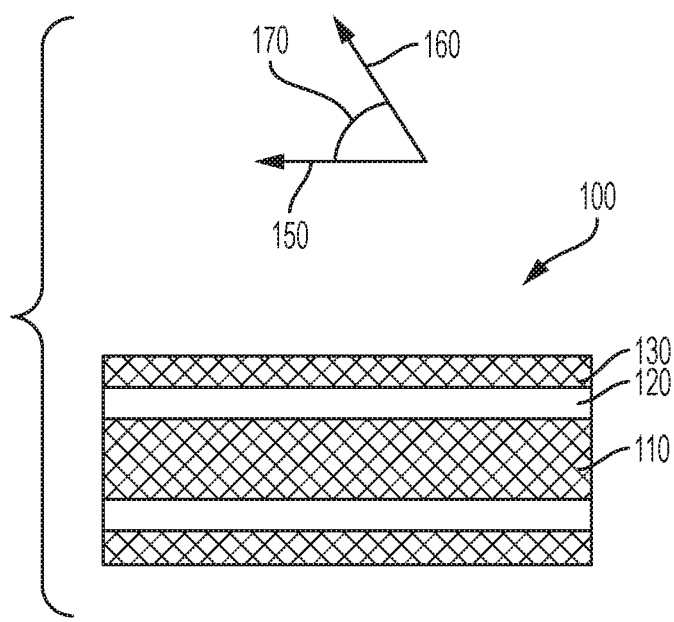
FIG. 3 illustrates a parallel section of an LDF in accordance with the present disclosure.

FIG. 3 shows a parallel section of the LDF 100 illustrated in FIG. 2. As shown, unscattered light propagates down the length of LDF 100 from the source in the direction shown by arrow 150. Scattered light, shown by arrow 160, exits LDF 100 at an angle 170, where the angle 170 describes angular difference between the direction of the fiber and the direction of the scattered light when it leaves LDF 100. The UV-visible spectrum of LDF 100 may be independent of angle 170. Alternatively, the intensities of the spectra when angle 170 is between about 20° and about 150° are within ±40% as measured at the peak wavelength. For example, the intensities of the spectra when angle 170 is between about 20° and about 150° may be within ±30%, or ±20%, or ±15%, or ±10%, or even ±5%, as measured at the peak wavelength.

Colored light can be emitted from the LDF 100 having an outer polymer coating layer 130 in accordance with the present disclosure by coupling the LDF 100 with a higher energy (lower wavelength) light source, such as a light source emitting at 405 nm or 445 nm. The light source may be configured to emit light having a wavelength of between about 300 nm and about 550 nm. The light source may be, for example, a diode laser. The light from the light source is emitted from the core portion 110 and causes the luminophore to fluoresce or phosphoresce such that the wavelength of the light emitted from the LDF 100 corresponds to a predetermined color. Where the luminophore includes a mixture of fluorescent or phosphorescent materials, the mixture may be modified and controlled such that the wavelength of the light emitted from the LDF 100 corresponds to a predetermined color.

In embodiments, colored light can be emitted from the LDF corresponding to the wavelengths of light used by plants in photosynthesis. For example chlorophyll-a utilizes light between 430 nm and 662 nm. Chlorophyll-b utilizes light between 453 nm and 642 nm. Carotenoids utilize light between 449 and 475 nm. In embodiments, the light source and the LDF are configured so that the LDF emits light at wavelengths between 430 nm and 662 nm. The presence of liquid or liquid media (which may contain colored pigments) inside the container may affect the passage of light through the container. Therefore, the user may need to adjust the wavelength of light delivered to the container depending upon the culture conditions inside the container to maximize the delivery of light at the appropriate wavelength to cells growing inside the container to reach desired cell growth results.

In additional embodiments, the LDF and the light source can be configured to emit light useful to sterilize the container. UV light, in the range of 200 nm to 280 nm may be delivered to the container via the LDF. In these embodiments the light source may be, for example, a UV laser. In such embodiments, a thicker diameter light source may be required, to provide a UV light source.

In embodiments, the LDF may be flexible, or stiff. For example, in embodiments, the LDF may be provided in bundles. The LDF affords a small, flexible light source that can be coupled to a laser or LED source. This small flexible fiber should be compatible with existing bioreactor systems. Such systems or containers may be vertical (see, for example, FIG. 7A), horizontal (see, for example, FIG. 7B), rigid or flexible. Red, green and blue light sources may be coupled together to afford light of almost any wavelength combination. The light source employed may be remote from the fiber and can be further removed by the use of transmission fiber. This allows the fiber to deliver light directly into an aqueous cell culture media contained in the container. Because the light source is the only source of heat and may be remote from the container, the fiber remains cool, allowing the fiber to reside inside the container without affecting the temperature of the contents of the container. This also allows the fiber to reside in a wall of the container, or wrapped around the container.

In embodiments, the fiber may be coupled to a detector which measures transmission changes (changes in optical density) to monitor cell growth. In embodiments, multiple fibers could be used to illuminate the container. In additional embodiments, multiple fibers, enough to illuminate the entire container may be used.

The fibers described herein may be formed utilizing various techniques. For example, the core 110 can be made by any number of methods which incorporate voids or particles into the glass fiber. For example, methods for forming an optical fiber preform with voids are described in, for example, U.S. Patent Application Publication No. 2007/0104437 A1, which is incorporated in its entirety herein by reference. Additional methods of forming voids may be found in, for example, U.S. Patent Application Publication No. 2011/0122646 A1, U.S. Patent Application Publication No. 2012/0275180 A1, and U.S. Patent Application Publication No. 2013/0088888 A1, which are incorporated in their entirety herein by reference.

According to embodiments of the present disclosure, a method for forming a light diffusing fiber includes forming an optical fiber preform having a preform core portion. The method may further include drawing the optical fiber preform to form an optical fiber and coating the optical fiber with an outer polymer coating layer that includes a scattering material and a luminophore.

The method may further include coating the optical fiber with a polymeric cladding layer that surrounds and is in direct contact with the core. Where the optical fiber is coated with a polymeric cladding layer, coating the optical fiber with the outer polymer coating layer includes coating the cladding layer with the outer polymer coating layer. Alternatively, the optical fiber preform may further include a silica-based glass cladding portion surrounding and in direct contact with the preform core portion. Such optical fiber preform may be drawn to form an optical fiber having a silica-based glass cladding, and coating the optical fiber with the outer polymer coating layer includes coating the silica-based glass cladding with the outer polymer coating layer.

Generally, the optical fiber is drawn from an optical fiber preform with a fiber take-up system and exits the draw furnace along a substantially vertical pathway. The fiber may be rotated as it is drawn to produce helical voids along the long axis of the fiber. As the optical fiber exits the draw furnace, a non-contact flaw detector may be used to examine the optical fiber for damage and/or flaws that may have occurred during the manufacture of the optical fiber. Thereafter, the diameter of the optical fiber may be measured with a non-contact sensor. As the optical fiber is drawn along the vertical pathway, the optical fiber may optionally be drawn through a cooling system which cools the optical fiber prior to the application of coatings to the optical fiber. After the optical fiber exits the draw furnace or optional cooling system, the optical fiber enters at least one coating system where one or more polymer layers are applied to the optical fiber. As the optical fiber exits the coating system, the diameter of the optical fiber may be measured with non-contact sensor. Thereafter, a non-contact flaw detector is used to examine the optical fiber for damage and/or flaws in the coating that may have occurred during the manufacture of the optical fiber.

EXAMPLES

Embodiments of the present disclosure are further described below with respect to certain exemplary and specific embodiments thereof, which are illustrative only and not intended to be limiting.

Table I illustrates characteristics and performance of various outer polymer coating layers in accordance with embodiments of the present disclosure. Light diffusing optical fibers 1-5 included outer polymer coating layers in accordance with the outer polymer coating layer 130 illustrated in FIG. 3. The outer polymer coating layer in each of fibers 1-5 was applied to an LDF that included a core portion, a cladding portion and a coating layer that was the cured product of a polymer material. As a comparison, light diffusing optical fibers 6-8 were conventional LDF including the various glass portions and polymer layers as the LDF illustrated in FIG. 2 with the outermost coating being a phosphor coating layer 14. For the outermost coating layer of each of the fibers, Table I shows concentration of scattering composition (wt. %), concentration of scattering material (wt. %) and concentration of luminophore (wt. %), in the liquid polymer blend. Table I shows the concentration of polymer material (wt. %) in the scattering composition and also the coating thickness (μm) of the cured coating layer. Table I also shows CIE 1931 x, y chromaticity space values for the color of the light emitted from each of the fibers.

TABLE I

| | Scattering Composition (wt. %) | Luminophore (wt. %) | Polymer Material (wt. %) | Scattering Material (wt. %) | Thickness (μm) | x | y |
|---|---|---|---|---|---|---|---|
| 1 | 15 | 28 | 57 | 0.75 | 90 | 0.365 | 0.445 |
| 2 | 15 | 28 | 57 | 0.75 | 140 | 0.39 | 0.49 |
| 3 | 10 | 30 | 60 | 0.50 | 90 | 0.345 | 0.405 |
| 4 | 30 | 23 | 47 | 1.50 | 90 | 0.31 | 0.34 |
| 5 | 40 | 20 | 40 | 2.00 | 50 | 0.28 | 0.25 |
| 6 | 0 | 33 | 67 | 0 | 25 | 0.27 | 0.23 |
| 7 | 0 | 33 | 67 | 0 | 100 | 0.3 | 0.3 |
| 8 | 0 | 33 | 67 | 0 | 190 | 0.36 | 0.41 |

Figure 4:
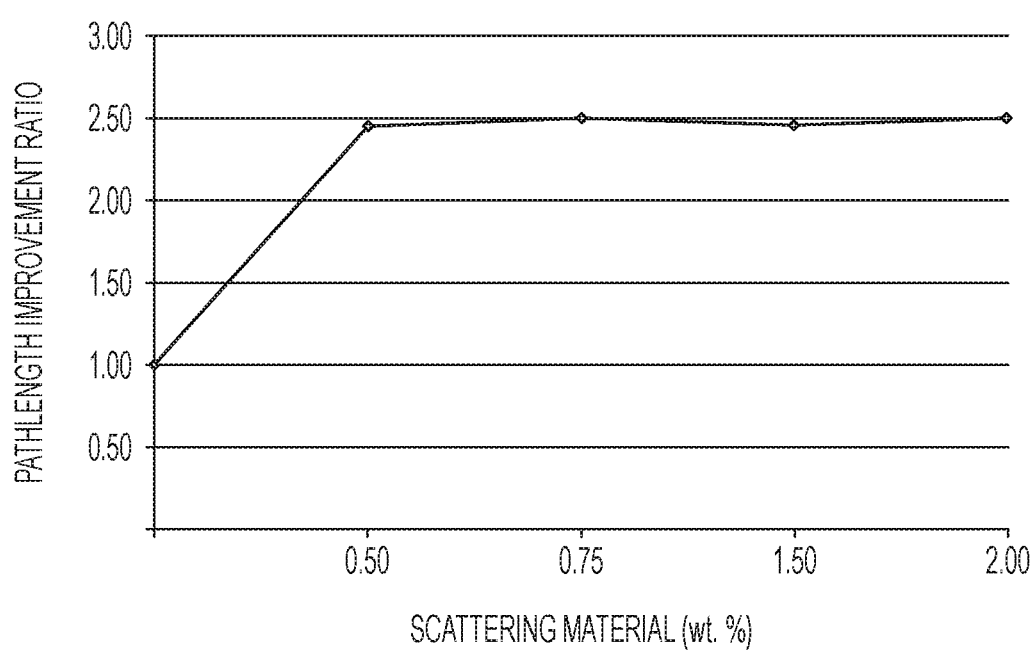
FIG. 4 is a graph showing the relationship of the improvement ratio of the path length of an excitation photon in a phosphor coating layer to the concentration of scattering material in light diffusing fibers according to embodiments of the present disclosure.

From the data in Table I, the path length of an excitation photon in the outermost coating layer was estimated and compared to the actual thickness of the outermost coating layer. FIG. 4 is a graph showing the relationship of the improvement ratio of the path length of an excitation photon in the outermost coating layer to the concentration of scattering material (wt. %) in light diffusing fibers according to embodiments of the present disclosure. As shown, where the outermost coating layer has a concentration of scattering material of about 0.50 wt. % or more, the path length of an excitation photon is more than 2.0 times greater than the actual thickness of the outermost coating layer.

Figure 5:
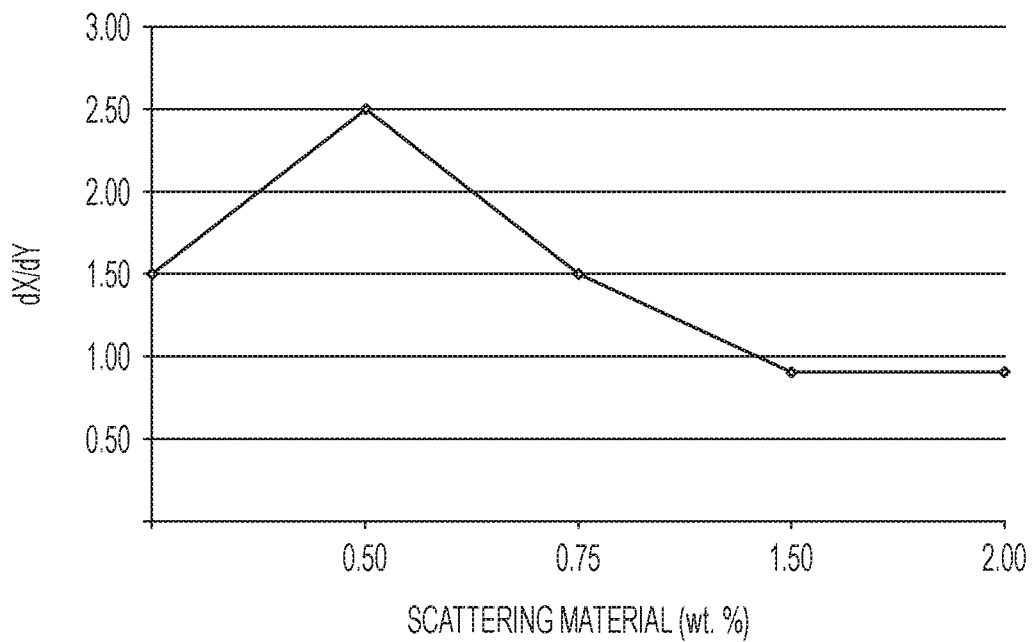
FIG. 5 is a graph showing the relationship of the ratio of change in the x chromaticity of CIE 1931 color space value/change in the y chromaticity of CIE 1931 color space value of the color of light emitted from the light diffusing fibers to the concentration of scattering material (wt. %) in the outermost coating layer.

Embodiments of the present disclosure provide LDF having reduced luminophore concentration in the coatings that emit light having the same color and the same or better uniformity as conventional LDF. Differences in the CIE 1931 x, y chromaticity space values for the color of the light emitted from light diffusing fibers at different viewing angles was observed and measured. FIG. 5 is a graph showing the relationship of the ratio of change in the x chromaticity of CIE 1931 color space value/change in the y chromaticity of CIE 1931 color space value of the color of light emitted from the light diffusing fibers to the concentration of scattering material (wt. %) in the outermost coating layer. The lower the ratio, the better the uniformity of the color of the emitted light. As shown, where the outermost coating layer has a concentration of scattering material of about 0.50 wt. % or more, the uniformity of the color of light emitted from the light diffusing fibers is the same or better than the conventional LDF having no scattering material in the outermost coating layer.

Figure 6:
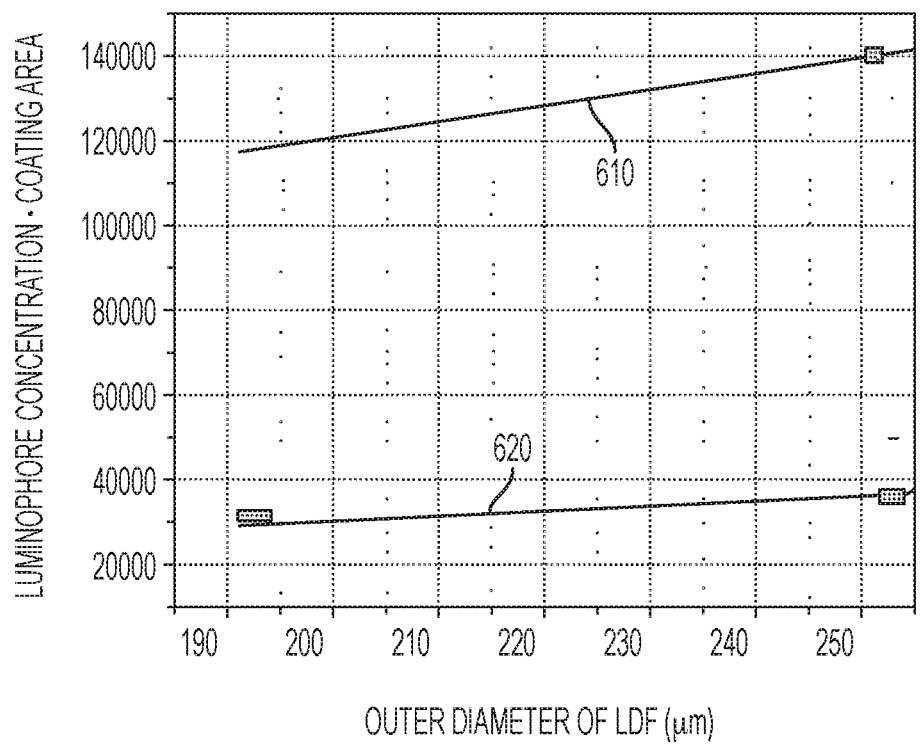
FIG. 6 is a graph showing the relationship of luminophore concentration in a luminophore-containing coating layer and the outer diameter of the cladding layer in two light diffusing fibers.

As less luminophore is needed in the outer polymer coating of LDF as described herein, the overall costs of the LDF are reduced. FIG. 6 is a graph showing the relationship of luminophore concentration in a luminophore-containing coating layer (illustrated with a value that is the result of luminophore concentration in the coating multiplied by the area of the coating) and the outer diameter of the LDF in two light diffusing fibers 610 and 620. The two fibers 610 and 620 were designed to emit light having a color that can be defined as 0.31:0.31 using CIE 1931 x, y chromaticity space values. Fibers 610 were conventional LDF, such as is illustrated in FIG. 1, having a phosphor coating layer 14 having a thickness of 120 μm. Fibers 620 were formed in accordance with the LDF illustrated in FIG. 2 and had an outer polymer coating layer 130 having a thickness of 40 μm. As is shown, for all cladding outer diameters between 190 μm and 260 μm, fibers 620 emitted light having the same color as fibers 610 with a reduced luminophore concentration. In particular, luminophore concentration of fibers 620 was between about 3.5 and about 5.0 times less than luminophore concentration of fibers 610.

Figure 7A:
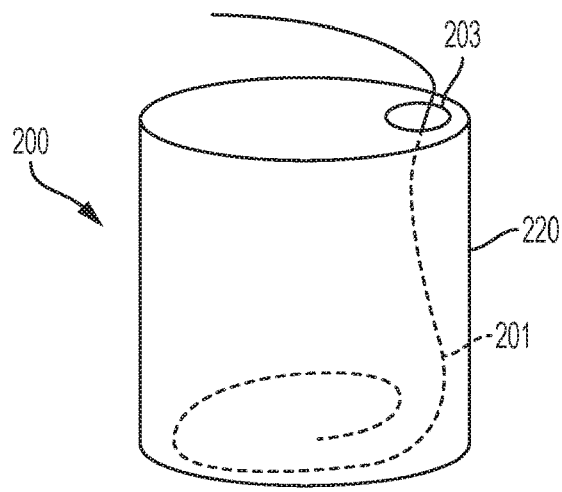
FIGS. 7A-C are drawings showing embodiments of deployment of LDF inside (FIG. 7A and 7B) and around (FIG. 7C) a container for the growth of biological entities.

FIGS. 7 A-C are illustrations of embodiments of illuminated containers for the growth of biological entities. In embodiments, the container may be rigid or flexible and may be in the form of a single well, a single well of a multi-well plate, a flask, a dish, a bag, a tank, a multi-layered flask, a bioreactor or a bioreactor. The container may be reusable or single-use. In embodiments the container may have at least one wall 220. The at least one wall 220 may be rigid or flexible. That is, the wall 220 may be the side of a bag or, as is shown in, for example, FIG. 7A, a single wall 220 of a cylindrical container. The container may have more than one wall 220 to form any suitable shape including square, cuboid, pyramidal, or any other shape. Any polymer (such as polystyrene, polycarbonate, acrylic, polystyrene, or polyester) suitable for molding and commonly utilized in the manufacture of laboratory ware may be used. In some embodiments, polystyrene is used. Separate parts, including multiple walls, may be assembled by any number of methods including but not limited to: adhesive or solvent bonding, heat sealing or welding, compression, ultrasonic welding, laser welding and/or any other method commonly used for generating seals between parts such that it becomes an integral portion of the interior surface of the container.

In embodiments, the container may have at least one port, or one access feature for delivering biological entities (optionally including media or water or other materials used when growing biological entities) to the container or removing biological entities from the container.

Figure 7B:
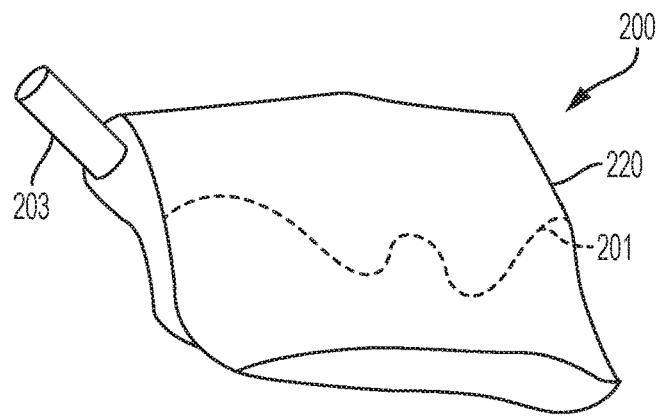
Figure 7C:
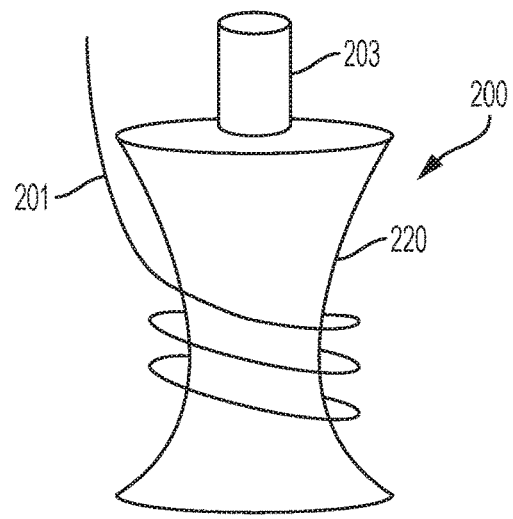

In FIG. 7A, a cylindrical container 200 is illustrated, with an LDF 201 inserted into the container 200 through a port 203 in the container. The LDF 201 is illustrated as a solid line outside the container, and a dashed line inside the container. In embodiments, the container may be of any size or shape. The container may have additional ports for the entry and exit of cells and media, and may be rigid or flexible. FIG. 7B is an illustration of a flexible bag 205 for the growth of biological entities having an LDF 201 inside the bag. FIG. 7C is an illustration of a flexible bag 205 embodiment having an LDF 201 wrapped around the outside of the bag. In the embodiment shown in FIG. 7C, but not in the embodiments shown in FIGS. 7A and 7B, the bag would need to be transparent in order for the light diffusing from the fiber to reach cells inside the bag. In embodiments, the bag 205, or the flexible container, may be made from polymeric material. In embodiments, the bag is made of layers of polymeric material. For example, the inside layer, the layer in contact with the contents of the bag, may be made from a material having low leachables and extractables, low cytotoxicity, low cell binding characteristics, resistance to chemical damage, and good water tight characteristics. Example materials are low density polyethylene (LDPE) or polypropylene (PP). A second layer provides gas permeability and flexibility. Example materials are polyvinyl alcohol (PVA) or polyvinyl chloride (PVC). An outer layer may be used to lend mechanical strength. Example materials are low density polyethylene (LDPE) or polyethylene terephthalate (PET). such as, for example, polypropylene, ethyl vinyl acetate, polyvinyl acetate. While these material examples are provided, those of ordinary skill in the art will recognize that any suitable material may be used.

In the embodiments shown in FIGS. 7A-C, a single fiber is shown, but multiple fibers may be provided in or on the container, in embodiments.

Figure 8A:
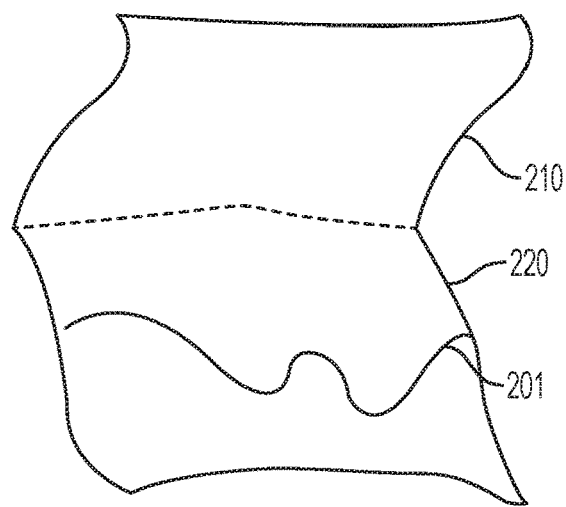
FIGS. 8A-C are drawings showing lamination of a LDF in a layer of polymer which forms a container for the growth of biological entities.
Figure 8B:
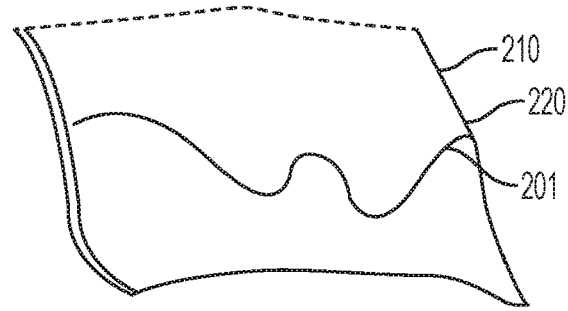
Figure 8C:
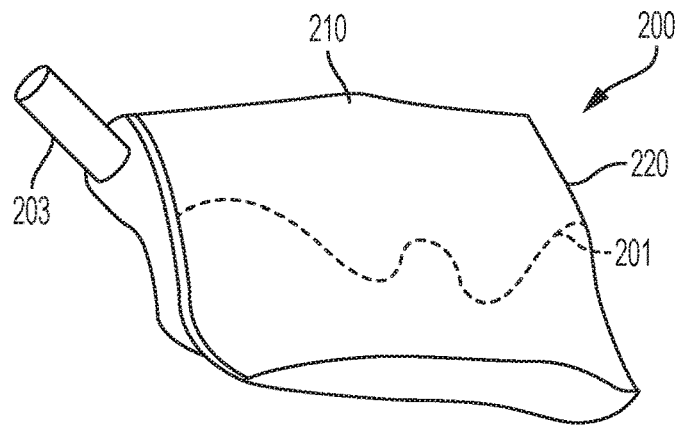

FIG. 8A-C illustrates an embodiment of a container where the light diffusing fiber is embedded within a wall 220 of a container. In FIG. 8A, an LDF 201 is placed on a sheet of polymer 210. In FIG. 8B, the sheet of polymer is folded around the LDF and melted or welded together. In FIG. 8C, a container, in this case a flexible bag, is shown, made from the polymer 201 containing the embedded LDF 201. In additional embodiments, additional layers of polymer may be melt pressed or welded together with the polymer having embedded LDF to form multiple layered containers.

Light might escape from the distal end of the LDF. In embodiments, this emitted light could be coupled to a detector to measure loss of light during transmission through the media in the container, and thus measure optical density to determine cell growth within the container.

According to an aspect (1) of the present disclosure, an illuminated container for the growth of biological entities is provided. The illuminated container comprises a container having at least one wall and a port, and a light diffusing fiber comprising a core formed from a silica-based glass, a cladding in direct contact with the core, and an outer polymer coating layer surrounding the light diffusing fiber, the outer polymer coating layer being the cured product of a liquid polymer blend comprising a scattering composition and a luminophore.

According to another aspect (2) of the present disclosure, the container of aspect (1) is provided, wherein the light diffusing fiber is flexible.

According to another aspect (3) of the present disclosure, the container of any of aspects (1)-(2) is provided, wherein the container is a well, a flask, a dish, a bag, a tank, a multi-layered flask, a bioreactor or a single use bioreactor.

According to another aspect (4) of the present disclosure, the container of any of aspects (1)-(3) is provided, wherein the light diffusing fiber is configured to deliver light having a wavelength in a range between 430 nm and 662 nm.

According to another aspect (5) of the present disclosure, the container of any of aspects (1)-(4) is provided, wherein the light diffusing fiber is configured to deliver light having a wavelength in a range between 200 nm to 280 nm.

According to another aspect (6) of the present disclosure, the container of any of aspects (1)-(5) is provided, wherein the light diffusing fiber is contained within the container.

According to another aspect (7) of the present disclosure, the container of aspect (6) is provided, wherein the light diffusing fiber is immersed into an aqueous cell culture media contained in the container.

According to another aspect (8) of the present disclosure, the container of any of aspects (1)-(4) is provided, wherein the light diffusing fiber is on the outside of the container.

According to another aspect (9) of the present disclosure, the container of any of aspects (1)-(4) is provided, wherein the light diffusing fiber is imbedded in a wall of the container.

According to another aspect (10) of the present disclosure, the container of any of aspects (1)-(9) is provided, wherein the outer polymer coating layer of the light diffusing fiber comprises a radial width of between about 1.0 μm and about 450 μm.

According to another aspect (11) of the present disclosure, the container of any of aspects (1)-(10) is provided, wherein the light diffusing fiber of comprises an outer diameter of less than or equal to about 250 μm.

According to another aspect (12) of the present disclosure, the container of any of aspects (1)-(11) is provided, wherein the scattering material comprises high refractive index materials.

According to another aspect (13) of the present disclosure, the container of aspect (12) is provided, wherein the high refractive index materials comprise metal oxide particles.

According to another aspect (14) of the present disclosure, the container of aspect (13) is provided, wherein the metal oxide particles are selected from the group consisting of particles of $TiO_2$, $ZnO$, $SiO_2$, $BaS$, $MgO$, $Al_2O_3$ and $Zr$.

According to another aspect (15) of the present disclosure, the container of aspect (13) is provided, wherein the metal oxide particles comprise particles of $TiO_2$.

According to another aspect (16) of the present disclosure, the container of any of aspects (1)-(15) is provided, wherein the liquid polymer blend comprises between about 0.5 wt. % and about 10 wt. % of the scattering material.

According to another aspect (17) of the present disclosure, the container of any of aspects (1)-(16) is provided, wherein the luminophore is selected from the group consisting of a fluorescent material, a phosphorescent material, and mixtures thereof According to another aspect (18) of the present disclosure, the container of any of aspects (1)-(17) is provided, wherein the luminophore is selected from the group consisting of Ce-doped YAG, Nd-doped YAG, rare earth oxide materials, quantum dots, nanoparticles, and metal-enhanced fluorescence of organic fluorophores.

According to another aspect (19) of the present disclosure, the container of any of aspects (1)-(18) is provided, wherein the liquid polymer blend comprises between about 10 wt. % and about 50 wt. % of the luminophore.

According to another aspect (20) of the present disclosure, the container of any of aspects (1)-(19) is provided, wherein the core of the light diffusing fiber comprises nano-sized structures.

According to another aspect (21) of the present disclosure, the container of aspect (20) is provided, wherein the nano-sized structures comprise gas-filled voids.

According to another aspect (22) of the present disclosure, the container of aspect (21) is provided, wherein the gas-filled voids are filled with a gas selected from the group of $SO_2$, $Kr$, $Ar$, $CO_2$, $N_2$, $O_2$ and mixture thereof According to another aspect (23) of the present disclosure, the container of aspect (20) is provided, wherein the nano-sized structures have a diameter of about 10 nm to about 1.0 μm.

It will be apparent to those skilled in the art that various modifications and variations can be made without departing from the spirit or scope of the present disclosure.

What is claimed is:

1. An illuminated container for the growth of biological entities comprising:
   a container having at least one wall and a port;
   a light diffusing fiber tunable to different wavelengths of light for growth of biological entities in the container, the light diffusing fiber comprising:
   a core formed from a silica-based glass;
   a cladding in direct contact with the core; and
   an outer polymer coating layer surrounding the cladding, the outer polymer coating layer being the cured product of a liquid polymer blend comprising a scattering composition and a luminophore, wherein the liquid polymer blend comprises between about 0.5 wt. % and about 10 wt. % of the scattering material and between about 10 wt. % and about 35 wt. % or less of the luminophore; and
   a detector arranged to measure light transmission of light emitted from the light diffusing fiber and passed through media in the container.

2. The container of claim 1, wherein the light diffusing fiber is flexible.

3. The container of claim 1, wherein the container is a well, a flask, a dish, a bag, a tank, a multi-layered flask, a bioreactor or a single use bioreactor.

4. The container of claim 1, wherein the light diffusing fiber is configured to deliver light having a wavelength in a range between 430 nm and 662 nm.

5. The container of claim 1, wherein the light diffusing fiber is configured to deliver light having a wavelength in a range between 200 nm to 280 nm.

6. The container of claim 1, wherein the light diffusing fiber is contained within the container.

7. The container of claim 6, wherein the light diffusing fiber is immersed into an aqueous cell culture media contained in the container.

8. The container of claim 1, wherein the light diffusing fiber is on the outside of the container.

9. The container of claim 1, wherein the light diffusing fiber is imbedded in a wall of the container.

10. The container of claim 1, wherein the outer polymer coating layer of the light diffusing fiber comprises a radial width of between about 1.0 μm and about 450 μm.

11. The container of claim 1, wherein the light diffusing fiber of comprises an outer diameter of less than or equal to 250 μm.

12. The container of claim 1, wherein the scattering material comprises high refractive index materials.

13. The container of claim 12, wherein the high refractive index materials comprise metal oxide particles.

14. The container of claim 13, wherein the metal oxide particles are selected from the group consisting of particles of $TiO_2$, ZnO, $SiO_2$, BaS, MgO, $Al_2O_3$ and Zr.

15. The container of claim of claim 13, wherein the metal oxide particles comprise particles of $TiO_2$.

16. The container of claim 1, wherein the luminophore is selected from the group consisting of a fluorescent material, a phosphorescent material, and mixtures thereof.

17. The container of claim 1, wherein the luminophore is selected from the group consisting of Ce-doped YAG, Nd-doped YAG, rare earth oxide materials, quantum dots, nanoparticles, and metal-enhanced fluorescence of organic fluorophores.

18. The container of claim 1, wherein the liquid polymer blend comprises between about 10 wt. % and about 50 wt. % of the luminophore.

19. The container of claim 1, wherein the core of the light diffusing fiber comprises nano-sized structures.

20. The container of claim 19, wherein the nano-sized structures comprise gas-filled voids.

21. The container of claim 20, wherein the gas-filled voids are filled with a gas selected from the group of $SO_2$, Kr, Ar, $CO_2$, $N_2$, $O_2$ and mixture thereof.

22. The container of claim 19, wherein the nano-sized structures have a diameter of about 10 nm to about 1.0 μm.

23. The container of claim 1, further comprising a cured coating between the cladding and the outer polymer coating layer, wherein the cured coating comprises a curable cross-linker, a curable diluent, and a polymerization initiator and wherein the cured coating has a lower refractive index than the outer polymer coating layer.

* * * * *